United States Patent [19]

Starch

[11] Patent Number: 6,121,373

[45] Date of Patent: Sep. 19, 2000

[54] METHOD OF MAKING THICK WATER-IN-SILICONE EMULSIONS

[75] Inventor: Michael Stephen Starch, Midland, Mich.

[73] Assignee: Dow Corning Corporation, Midland, Mich.

[21] Appl. No.: 09/167,466

[22] Filed: Oct. 7, 1998

[51] Int. Cl.[7] ............................ C08L 83/06; C08K 5/541; A61K 7/00

[52] U.S. Cl. ......................... 524/837; 524/266; 524/863; 424/78.02; 523/102

[58] Field of Search ..................................... 524/837, 863, 524/266; 523/102; 424/78.02

[56] References Cited

U.S. PATENT DOCUMENTS

| | | | |
|---|---|---|---|
| 5,302,382 | 4/1994 | Kasprzak | 424/78 |
| 5,330,747 | 7/1994 | Krzysik | 424/63 |
| 5,399,342 | 3/1995 | Krzysik | 424/59 |
| 5,443,760 | 8/1995 | Kasprzak | 424/78 |
| 5,599,533 | 2/1997 | Stepniewski | 524/78 |
| 5,654,362 | 8/1997 | Schulz | 524/862 |
| 5,665,804 | 9/1997 | Hill | 524/268 |
| 5,939,478 | 8/1999 | Beck et al. | 524/837 |

*Primary Examiner*—Tae Yoon
*Attorney, Agent, or Firm*—James L. De Cesare

[57] ABSTRACT

Thickening can be obtained by adding a silicone latex to the water phase of a water-in-silicone emulsion, instead of adding the silicone latex to the silicone phase of the emulsion. The latex is used in a range of about 0.1–5.0% by weight. Thick emulsions are made by (i) separately preparing a silicone phase containing a silicone polyether and a cyclic siloxane; (ii) separately preparing an aqueous phase containing water and at least one active ingredient; (iii) adding the latex to the aqueous phase; and (iv) combining and mixing the phases.

9 Claims, No Drawings

METHOD OF MAKING THICK WATER-IN-SILICONE EMULSIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to a method of making thick water-in-silicone emulsions, and more particularly to water-in-silicone emulsions thickened with a silicone latex.

BACKGROUND OF THE INVENTION

Thick water-in-silicone emulsions are useful in a number of personal care consumer products including antiperspirants, pigmented products such as liquid foundations, hair dressings, and skin moisturizers. Prior to the present invention, water-in-silicone emulsions were thickened by the addition of high-molecular weight silicones to the silicone phase of an emulsion.

Surprisingly, and contrary to conventional wisdom, it has now been discovered that dramatic thickening can be achieved by addition of a silicone latex to the water phase of a water-in-silicone emulsion, instead of adding a silicone latex to the silicone phase of the emulsion.

The addition of the silicone latex to the water phase provides several processing advantages. Since the latex is a water-based dispersion, it is most easily combined with the water phase prior to the preparation of the emulsion. Another advantage is that swelling of the latex particles is delayed until the silicone and water phases are brought together during emulsification. This keeps the viscosity of the two phases low and thereby facilitates processing.

The silicone latex is useful as a thickening additive when employed in a range of about 0.1 to 5.0 percent by weight of the emulsion. The amount of silicone latex depends upon the desired viscosity, and the phase volume ratio between the water phase and the silicone phase. The inherent viscosity of such an emulsion system without a thickener is determined primarily by the proportion of the water phase. The addition of a silicone latex to the water phase of the emulsion provides thickening over a range of different phase volume ratios.

BRIEF SUMMARY OF THE INVENTION

The present invention relates to a method of making a water-in-silicone emulsion by (i) preparing a silicone phase containing a silicone polyether and a cyclic siloxane; (ii) preparing an aqueous phase containing water and at least one cosmetically acceptable personal care component as an active ingredient; (iii) adding a silicone latex to the aqueous phase; (iv) combining the silicone phase with the aqueous phase containing the silicone latex; and (v) mixing the phases until an emulsion is formed.

Cosmetically acceptable personal care components generally include materials which are soluble in the aqueous phase, such as an antiperspirant salt, a humectant, an organic surfactant, an electrolyte, or a preservative.

In a preferred embodiment, the silicone phase also contains a silicone elastomer which is a composition prepared by a crosslinking reaction between an ≡Si—H containing polysiloxane and an alpha, omega-diene, carried out in the presence of a platinum catalyst and a cyclic siloxane.

The invention is also directed to water-in-silicone emulsions prepared according to this method.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

Water-in-silicone emulsions according to the present invention include a silicone phase and an aqueous or water phase. The silicone phase generally comprises 20–80 percent by weight of the emulsion, and the water phase generally comprises 20–80 percent by weight of the emulsion, based on the total weight of the emulsion.

The silicone phase preferably contains 0.2–2.0 percent by weight of a silicone polyether; 0–20 percent by weight of a suitable emollient, where the emulsion is intended for skin care application; 0–20 percent by weight of a pigment or a mixture of pigments, where the emulsion is intended for cosmetic application; with the balance of the silicone phase to 100 percent being comprised of a volatile cyclic siloxane.

The water phase preferably contains 0.1–5.0 percent by weight of a silicone latex; 5–30 percent by weight of an antiperspirant salt active, where the emulsion is intended for underarm application; 0.1–1.0 percent by weight of a suitable preservative; 0–15 percent by weight of a humectant; 0–4 percent by weight of an electrolyte; 0–0.5 percent by weight of an organic nonionic emulsifying agent; with the balance of the aqueous phase to 100 percent being deionized water.

The humectant should be a composition that is also capable of functioning as an agent for adjusting the refractive index of the two phases, to provide optical clarity or at least translucency, when this type of appearance is desirable, e.g., when the emulsion is packaged in a clear container. It should also be a composition that will hold pigments to the skin, when the emulsion is intended for cosmetic application. Propylene glycol is one example of a composition suitable for such purposes.

As used herein, the term "silicone latex" is intended to mean a silicone emulsion which yields an elastomer upon water evaporation. An especially preferred silicone latex is a composition described in U.S. Pat. No. 5,665,804 (Sep. 9, 1997), the contents of which is considered incorporated by reference.

This silicone latex is prepared by a method which comprises:

(A) mixing (i) 100 weight parts of a siloxane polymer having a viscosity of greater than 5,000 mPa·s but less than 500,000 mPa·s at 25° C., (ii) 0.5–10 weight parts of a surfactant, and (iii) 0.5–25 weight parts of water; (B) emulsifying the mixture into a gel phase having a siloxane polymer content of at least 80% by weight; (C) diluting the emulsion with further water to a siloxane polymer content of at least 75% by weight; (D) adding 0.00001–20 weight parts catalyst either before or after the emulsification, or before or after the dilution; (E)

adding 0.1–20 weight parts crosslinker either before or after the emulsification, or before or after the dilution; and (F) or in place of adding (D) and (E), adding 1–5 weight parts self catalytic crosslinker, either before or after emulsification, or before or after dilution.

These silicone latex compositions typically have a solids content of siloxane polymer of at least 75 percent by weight. The siloxane polymer has the formula $X_{3-n}R_n$—YO—$(R^1{}_2SiO)_z$—Y—$R_nX_{3-n}$ where n is 0, 1, 2 or 3; z is an integer from 500–5,000; X is hydrogen, a vinyl group, a hydroxyl group, a condensable or hydrolyzable group; Y is a silicon atom, the group $\equiv$Si—$(CH_2)_m$—$SiR^1{}_2$—, or the group $\equiv$Si—$(CH_2)_m$—$SiR^1{}_2OSiR^1{}_2(CH_2)_m$—$SiR^1{}_2$—, where m is 1–8; R is an aliphatic alkyl, aminoalkyl, polyaminoalkyl, epoxyalkyl, alkenyl, or aromatic group; and $R^1$ is X, an aliphatic alkyl, alkenyl, or an aromatic group.

Most preferred are the siloxane polymers having at least two vinyl groups per molecule bonded to a silicon atom. The crosslinker should have an average of at least two silicon-bonded hydrogen atoms, and it should be a silicon hydride crosslinker present in an amount sufficient to provide at least one hydrogen atom for each vinyl group in the siloxane polymer.

The catalyst is normally a noble metal catalyst, but where a self catalyzing crosslinker is used, it should have at least one catalytic leaving group such as acetoxy, amide, acetamide, aminoxy, or oxime. Some suitable self catalyzing crosslinkers are compositions with formula:

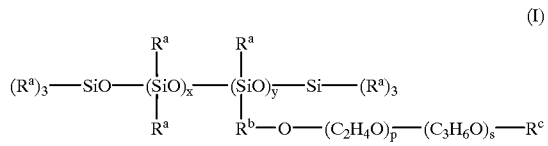

where R is the same or a different alkyl group of 1–8 carbon atoms; a is zero or a positive integer; and b is greater than two.

The surfactant used in emulsifying the silicone latex can be a nonionic surfactant, cationic surfactant, anionic surfactant, amphoteric surfactant, or mixtures thereof. In the present invention, however, a nonionic surfactant is most preferred.

This silicone latex component of the water phase of the emulsion is shown in Tables 1 and 2 as the "Silicone Latex (75% Elastomer)".

An example of silicone polyethers suitable for use in the present invention are compositions having the formula:

(I)

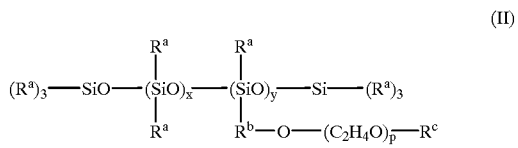

where $R^a$ is an alkyl group of one to six carbon atoms; $R^b$ is the radical —$C_mH_{2m}$—; $R^c$ is a terminating radical such as hydrogen, an alkyl group of one to six carbon atoms, or an aryl group such as phenyl; m has a value of two to eight; p and s have values such that the oxyalkylene segment —$(C_2H_4O)_p$—$(C_3H_6O)_s$— has a molecular weight in the range of 400 to 5,000; the segment preferably having 50–99 mole percent of oxyethylene units —$(C_2H_4O)_p$— and 1–50 mole percent of oxypropylene units —$(C_3H_6O)_s$—; x has a value of 80 to 400; and y has a value of 2 to 10.

Preferably, $R^a$ and the terminating radical $R^c$ are methyl groups; m is preferably three or four whereby the group $R^b$ is most preferably —$(CH_2)_3$—; and the values of p and s provide a molecular weight of oxyalkylene segment —$(C_2H_4O)_p$—$(C_3H_6O)_s$— of between 1,000 to 3,000. Most preferably, p and s each have a value of about 18 to 28.

Another example of a similar and useful silicone polyether is a composition having the formula:

(II)

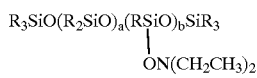

where $R^a$ is an alkyl group of one to six carbon atoms; $R^b$ is the radical —$C_mH_{2m}$—; $R^c$ is a terminating radical such as hydrogen, an alkyl group of one to six carbon atoms, or an aryl group such as phenyl; m has a value of two to eight; p has a value of 8 to 16; x has a value of 6 to 12; and y has a value of 1 to 8.

In Formula (I) or Formula (II), the silicone polyethers, i.e., siloxane-oxyalkylene copolymers, may take the form of endblocked polyethers in which the linking group $R^b$, the oxyalkylene segments, and the terminating radical $R^c$, occupy positions bonded to the ends of the siloxane chain, rather than being bonded to a silicon atom in the siloxane chain.

Thus, one or more of the $R^a$ substituents attached to the two terminal silicon atoms at the end of the siloxane chain, can be substituted with the segment —$R^b$—O—$(C_2H_4O)_p$—$(C_3H_6O)_s$—$R^c$ or with the segment —$R^b$—O—$(C_2H_4O)_p$—$R^c$.

In some instances, it may be desirable to provide these segments in the siloxane chain itself, as well as at one or both of the ends of the chain.

Methods for making such silicone polyethers are known in the art, and are described in detail in standard texts such as Chemistry & Technology of Silicones, Walter Noll, Academic Press Inc., 1968, Pages 373–376.

Silicone polyether are commercially available as blends containing about 10–13 percent by weight of the silicone polyether as the active ingredient, and about 87–90 percent by weight of a cyclic silicone such as octamethylcyclotetrasiloxane, decamethylcyclopentasiloxane, or mixtures of cyclic siloxanes.

This component of the silicone phase of the emulsion is shown in Tables 1 and 2 as the Silicone Polyether & $D_5$ Cyclic Siloxane (10% Polyether).

Cyclic siloxanes useful in making emulsions according to this invention are siloxane oligomers of the formula $(R_2SiO)_x$ where each R is a saturated alkyl group of 1–6 carbon atoms or an aryl group, and x is 3–7. Suitable R groups are methyl, ethyl, propyl, and phenyl. Cyclic siloxanes most preferred include hexamethylcyclotrisiloxane ($D_3$), octamethylcyclotetrasiloxane ($D_4$), decamethylcyclopentasiloxane ($D_5$), dodecamethylcyclohexasiloxane ($D_6$), and mixtures of such oligomers.

This component of the silicone phase of the emulsion is shown in Tables 1 and 2 as the "$D_5$ Cyclic Siloxane".

Emollients which can be employed in this invention include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic acid; fatty alcohols such as lauryl, myristyl, cetyl, stearyl, isostearyl, oleyl, ricinoleyl, erucyl, and 2-octyl dodecanol; lanolin and derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; hydrocarbons such as petrolatum and squalane; and silicones.

Representative silicones useful as emollients in preparing emulsions according to this invention are film forming organic polysiloxanes having a viscosity in a range of about 5 to as high as several million mPa·s, but preferably from about 100 to about 10,000 mPa·s. Mixtures of such polysiloxanes having relatively higher and relatively lower viscosities can also be employed. These polysiloxanes have repeating units

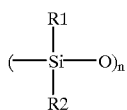

where n is an integer having a value greater than one; R1 is an alkyl radical containing 1 to 7 carbon atoms, or a phenyl group; $R_2$ is hydrogen, an alkyl radical containing 1 to 7 carbon atoms, or a phenyl group.

Illustrative polysiloxanes are polydimethylsiloxane, polydiethylsiloxane, polymethylethylsiloxane, polymethylphenylsiloxane, polydiphenylsiloxane, and diphenylsilanediol.

These silicones can be blended with silicone resins, and one useful composition comprises a polydimethylsiloxane fluid having a viscosity of about one hundred mPa·s mixed with trimethylsiloxysilicate, an MQ resin having the formula $[(CH_3)_3SiO_{1/2}]_x[SiO_{4/2}]_y$, in which x and y are positive integers.

Another useful silicone composition useful as an emollient are ultra-high viscosity silicone gums. Such gums typically have a structure corresponding to $HOMe_2SiO(Me_2SiO)_nSiMe_2OH$ in which Me is methyl, and n is 1–10,000. Because of the high viscosity of silicone gums, they are often provided as blends with other silicones such as $D_4$ or linear silicone fluids having a viscosity of 5–350 mPa·s.

Another useful silicone emollient, and the emollient used in the accompanying examples, is a silicone elastomer which is a composition described in U.S. Pat. No. 5,654,362 (Aug. 5, 1997), incorporated herein by reference. Such compositions are prepared by a crosslinking reaction between an ≡Si—H containing polysiloxanes and an alpha, omega-diene, in the presence of a platinum catalyst and a cyclic siloxane. The composition consists of a silicone elastomer swollen with the cyclic siloxane.

In particular, these elastomeric compositions can be prepared by reacting (A) an ≡Si—H containing polysiloxane of formula $R_3SiO(R'_2SiO)_a(R''HSiO)_bSiR_3$, and optionally an ≡Si—H containing polysiloxane of formula $HR_2SiO(R'_2SiO)_cSiR_2H$ or formula $HR_2SiO(R'_2SiO)_a(R''HSiO)_bSiR_2H$, where R, R', and R'' are alkyl groups with 1–6 carbon atoms, a is 0–250, b is 1–250, and c is 0–250; with (B) an alpha, omega-diene of formula $CH_2=CH(CH_2)_xCH=CH_2$ where x is 1–20. The reaction is conducted in the presence of a platinum catalyst and (C) any low molecular weight silicone oil or other solvent.

This component of the silicone phase of the emulsion is shown in Table 1 as the "Silicone Elastomer & $D_5$ Cyclic Siloxane (13% Elastomer)".

Pigments useful herein include any U.S. Government Food & Drug Administration (FDA) certified inorganic and organic dye and lake such as carmine, chromium oxide, carbon black, iron oxide, mica, titanium oxide, titanium dioxide, ultramarine, zinc oxide, bismuth oxychloride, D & C Blue No. 1, D & C Orange No. 5, D & C Red No. 6 Aluminum Lake, D & C Red No. 7 Calcium Lake, D & C Green No. 8, D & C Red No. 17, FD & C Blue No. 1, FD & C Red No. 3, FD & C Yellow No. 6, and External D & C Violet No. 2. An especially preferred pigment and the pigment used in the accompanying examples, is a mixture of pigments carried in decamethylcyclopentasiloxane. The pigment mix contained about 60 percent by weight of $D_5$, about 16 percent of titanium dioxide, and about 8 percent by weight of each of red iron oxide, yellow iron oxide, and black iron oxide. These pigments were surface treated with a silicone to render them hydrophobic.

This component of the silicone phase of the emulsion is shown in Table 2 as the "Pigment Mix".

Since emulsions are susceptible to microbiological contamination, a preservative is generally required. Some suitable compositions include formaldehyde, 1,3-dimethylol-5,5-dimethyl (DMDM) hydantoin, 5-bromo-5-nitro-1,3-dioxane, methyl paraben, propyl paraben, sorbic acid, imidazolidinyl urea, and 5-chloro-2-methyl-4-isothiazolin-3-one which is sold under the tradename KATHON CG by Rohm & Haas Company, Philadelphia, Pennsylvania.

Useful humectants include polyhydroxy alcohols such as sorbitol, glycerin, hexylene glycol, propylene glycol, and hexanetriol; sugar and starch derivatives such as alkoxylated glucose and hydrolyzed mucopolysaccharides; D-panthenol, hyaluronic acid, lactamide monoethanolamine, acetamide monoethanolamine, urea, guanidine, glycolic acid, glycolate salts, lactic acid, and lactate salts; or mixtures thereof. Most preferred are glycerin, propylene glycol, urea, hydrolyzed collagen, and sodium pyroglutamate ($C_5H_7NO_3Na$).

Divalent and trivalent salts may be used as an electrolyte, and some examples of suitable salts are sodium chloride, magnesium chloride, aluminum chloride, and ammonium chloride. Sodium borate and antiperspirant salts such as aluminum chlorohydrate and aluminum-zirconium chlorohydrate can also be used. When present, these compositions aid in reducing the particle size of silicones in an emulsion, the net effect of which is a thickening of the overall composition.

While any type of surfactant may be used, nonionic surfactants having a hydrophilic-lipophilic balance (HLB) of 10–20 are preferred. Nonionic surfactants with HLB of less than 10 may be used, but hazy solutions often result due to limited solubility of the nonionic surfactant in water. When using nonionic surfactants with HLB less than 10, nonionic surfactants with HLB greater than 10 should be added.

Commercial nonionic surfactants are exemplified by 2,6, 8-trimethyl-4-nonyloxy polyethylene oxyethanols (6EO) and (10EO) sold under trademarks TERGITOL® TMN-6 and TERGITOL® TMN-10; alkyleneoxy polyethylene oxyethanol ($C_{11-15}$ secondary alcohol ethoxylates 7EO, 9EO, and 15EO) sold under trademarks TERGITOL® 15-S-7, TERGITOL® 15-S-9, TERGITOL® 15-S-15; other $C_{11-15}$ secondary alcohol ethoxylates sold under trademarks TERGITOL® 15-S-12, 15-S-20, 15-S-30, 15-S-40; and octylphenoxy polyethoxy ethanol (40EO) sold under trademark TRITON® X-405. All of these surfactants are products of Union Carbide Corporation, Danbury, Connecticut.

Some other commercial nonionic surfactants are nonylphenoxy polyethoxy ethanol (10EO) sold under tradename MAKON 10 by Stepan Company, Northfield, Ill. The nonionic surfactant used in the accompanying examples is polyoxyethylene 7 lauryl alcohol (Laureth-7), sold under tradename Rhodasurf L790, by Rhone-Poulenc (N.J.) Surfactant & Specialty Division, Cranberry, N.J. Polyoxyethylene 23 lauryl ether (Laureth-23) sold under tradename BRIJ 35L by ICI Surfactants, Wilmington, Del., can also be used.

When the emulsion is intended for use in underarm applications, it can contain any active salt such as aluminum dichlorohydrate, aluminum sesquichlorohydrate, aluminum-zirconium trichlorohydrex-gly, aluminum-zirconium tetrachlorohydrex-gly (AZG) aluminum-zirconium pentachlorohydrex-gly, and aluminum-zirconium octachlorohydrex-gly.

EXAMPLES

The following examples illustrate the invention in more detail.

Examples 1–3

Three translucent water-in-silicone antiperspirant emulsion gels were prepared containing a silicone phase and a water phase as shown in Table 1. In each example, the silicone phase and the water phase were prepared in separate containers by mixing the ingredients at room temperature (i.e., 20–25° C.) until uniform. The water phase was then slowly added to the silicone phase in a tall 1000 mL glass beaker, and mixed at 200–400 rpm with a laboratory mixer having a 2 inch turbine and a 2 inch propeller. As the liquid level rose to cover the top of the mixing blade, the mixer speed was increased to about 1380 rpm. After all of the water phase had been added, mixing was continued for ten minutes. During mixing, a spatula was used to scrape the walls of the beaker to aid in turning over the batch.

TABLE 1

Water-In-Silicone Antiperspirant Emulsion Gels

| | Comparative Example 1 | | Comparative Example 2 | | Example 3 | |
|---|---|---|---|---|---|---|
| | Wt % | Grams | Wt % | Grams | Wt % | Grams |
| Silicone Phase: | | | | | | |
| Silicone Elastomer & $D_5$ Cyclic Siloxane (13% Elastomer) | 3.5 | 17.5 | 0.0 | 0.0 | 0.0 | 0.0 |
| Silicone Polyether & $D_5$ Cyclic Siloxane (10% Polyether) | 10.0 | 50.0 | 10.0 | 50.0 | 10.0 | 50.0 |
| $D_5$ Cyclic Siloxane | 3.5 | 17.5 | 7.0 | 35.0 | 6.5 | 32.5 |
| Water Phase: | | | | | | |
| Antiperspirant Salt (35% AZG in Water) | 71.4 | 357.0 | 71.4 | 357.0 | 71.2 | 356.2 |
| Silicone Latex (75% Elastomer) | 0.0 | 0.0 | 0.0 | 0.0 | 0.7 | 3.4 |
| Propylene Glycol (Humectant) | 11.6 | 58.0 | 11.6 | 58.0 | 11.6 | 58.0 |
| Total | 100.0 | 500.0 | 100.0 | 500.0 | 100.0 | 500.0 |

The viscosity of the water-in-silicone antiperspirant emulsion gels were measured on a Brookfield "Helipath" viscometer equipped with a "T" spindle C No. 93 at 2.5 rpm. The viscosity of the emulsion gel in Example 1 was 141,500 mPa·s. The viscosity of the emulsion gel in Example 2 was 58,500 mPa·s. The viscosity of the emulsion gel in Example 3 was 151,300 mPa·s. The emulsion having the highest viscosity was the emulsion of Example 3 in which the silicone latex was added to the water phase.

Examples 4–6

The procedure used in Examples 1–3 was repeated to prepare three water-in-silicone pigment cosmetic emulsions suitable for use as liquid foundations. The content of the silicone phase and the water phase are shown in Table 2.

TABLE 2

Water-In-Silicone Pigment Emulsions

| | Comparative Example 4 | | Comparative Example 5 | | Example 6 | |
|---|---|---|---|---|---|---|
| | Wt % | Grams | Wt % | Grams | Wt % | Grams |
| Silicone Phase: | | | | | | |
| Silicone Latex (75% Elastomer) | 0.0 | 0.0 | 2.5 | 7.5 | 0.0 | 0.0 |
| $D_5$ Cyclic Siloxane | 3.3 | 9.9 | 0.8 | 2.4 | 0.8 | 2.4 |
| Silicone Polyether & $D_5$ Cyclic Siloxane (10% Polyether) | 7.5 | 22.5 | 7.5 | 22.5 | 7.5 | 22.5 |
| Pigment Mix | 34.0 | 102.0 | 34.0 | 102.0 | 34.0 | 102.0 |
| Water Phase: | | | | | | |
| Methyl Paraben (Preservative) | 0.1 | 0.4 | 0.1 | 0.4 | 0.1 | 0.4 |
| Propylene Glycol (Humectant) | 8.0 | 24.0 | 8.0 | 24.0 | 8.0 | 24.0 |
| Sodium Chloride (Electrolyte) | 1.0 | 3.0 | 1.0 | 3.0 | 1.0 | 3.0 |
| Laureth-7 Nonionic Surfactant (Rhodasurf L-790) | 0.1 | 0.3 | 0.1 | 0.3 | 0.1 | 0.3 |
| Silicone Latex (75% Elastomer) | 0.0 | 0.0 | 0.0 | 0.0 | 2.5 | 7.5 |
| Deionized Water | 46.0 | 137.9 | 46.0 | 137.9 | 46.0 | 137.9 |
| Total | 100.0 | 300.0 | 100.0 | 300.0 | 100.0 | 300.0 |

The viscosity of the emulsion in Example 4 was 300 mPa·s. The viscosity of the emulsion in Example 5 was 166,300 mPa·s. The viscosity of the emulsion in Example 6 was 174,600 mPa·s. The emulsion with the highest viscosity was the emulsion of Example 6 in which the silicone latex was added to the water phase.

Examples 7–13

The procedure used in Examples 1–3 was again repeated to prepare seven water-in-silicone moisturizing emulsions suitable for use as skin conditioners. Glycerin was the active ingredient present in these compositions. The content of the silicone phase and the water phase are shown in Tables 3–5.

TABLE 3

Water-In-Silicone Moisturizing Emulsions

| | Comparative Example 7 | | Example 8 | | Example 9 | |
|---|---|---|---|---|---|---|
| | Wt % | Grams | Wt % | Grams | Wt % | Grams |
| Silicone Phase: | | | | | | |
| $D_5$ Cyclic Siloxane | 20.0 | 60.0 | 20.0 | 60.0 | 20.0 | 60.0 |
| Silicone Polyether & $D_5$ Cyclic Siloxane (10% Polyether) | 10.0 | 30.0 | 10.0 | 30.0 | 10.0 | 30.0 |
| Water Phase: | | | | | | |
| DMDM Hydantoin (Preservative) | 0.5 | 1.5 | 0.5 | 1.5 | 0.5 | 1.5 |

TABLE 3-continued

Water-In-Silicone Moisturizing Emulsions

|  | Comparative Example 7 | | Example 8 | | Example 9 | |
| --- | --- | --- | --- | --- | --- | --- |
|  | Wt % | Grams | Wt % | Grams | Wt % | Grams |
| Glycerin (Humectant) | 5.0 | 15.0 | 5.0 | 15.0 | 5.0 | 15.0 |
| Sodium Chloride (Electrolyte) | 1.0 | 3.0 | 1.0 | 3.0 | 1.0 | 3.0 |
| Silicone Latex (75% Elastomer) | 0.0 | 0.0 | 0.5 | 1.5 | 1.0 | 3.0 |
| Deionized Water | 63.5 | 190.5 | 63.0 | 189.0 | 62.5 | 187.5 |
| Total | 100.0 | 300.0 | 100.0 | 300.0 | 100.0 | 300.0 |

The viscosity of the emulsion in Example 7 which contained none of the silicone latex was 4,933 mPa·s. The viscosity of the emulsion in Example 8 was 11,200 mPa·s. The viscosity of the emulsion in Example 9 was 26,114 mPa·s.

TABLE 4

Water-In-Silicone Moisturizing Emulsions

|  | Example 10 | | Example 11 | |
| --- | --- | --- | --- | --- |
|  | Wt % | Grams | Wt % | Grams |
| Silicone Phase: | | | | |
| $D_5$ Cyclic Siloxane | 20.0 | 60.0 | 20.0 | 60.0 |
| Silicone Polyether & $D_5$ Cyclic Siloxane (10% Polyether) | 10.0 | 30.0 | 10.0 | 30.0 |
| Water Phase: | | | | |
| DMDM Hydantoin (Preservative) | 0.5 | 1.5 | 0.5 | 1.5 |
| Glycerin (Humectant) | 5.0 | 15.0 | 5.0 | 15.0 |
| Sodium Chloride (Electrolyte) | 1.0 | 3.0 | 1.0 | 3.0 |
| Silicone Latex (75% Elastomer) | 1.5 | 4.5 | 2.0 | 6.0 |
| Deionized Water | 62.0 | 186.0 | 61.5 | 184.5 |
| Total | 100.0 | 300.0 | 100.0 | 300.0 |

The viscosity of the emulsion in Example 10 was 55,029 mPa·s. The viscosity of the emulsion in Example 11 was 101,760 mPa·s.

TABLE 5

Water-In-Silicone Moisturizing Emulsions

|  | Example 12 | | Example 13 | |
| --- | --- | --- | --- | --- |
|  | Wt % | Grams | Wt % | Grams |
| Silicone Phase: | | | | |
| $D_5$ Cyclic Siloxane | 20.0 | 60.0 | 20.0 | 60.0 |
| Silicone Polyether & $D_5$ Cyclic Siloxane (10% Polyether) | 10.0 | 30.0 | 10.0 | 30.0 |
| Water Phase: | | | | |
| DMDM Hydantoin (Preservative) | 0.5 | 1.5 | 0.5 | 1.5 |

TABLE 5-continued

Water-In-Silicone Moisturizing Emulsions

|  | Example 12 | | Example 13 | |
| --- | --- | --- | --- | --- |
|  | Wt % | Grams | Wt % | Grams |
| Glycerin (Humectant) | 5.0 | 15.0 | 5.0 | 15.0 |
| Sodium Chloride (Electrolyte) | 1.0 | 3.0 | 1.0 | 3.0 |
| Silicone Latex (75% Elastomer) | 2.5 | 7.5 | 3.0 | 9.0 |
| Deionized Water | 61.0 | 183.0 | 60.5 | 181.5 |
| Total | 100.0 | 300.0 | 100.0 | 300.0 |

The viscosity of the emulsion in Example 12 was 138,960 mPa·s. The viscosity of the emulsion in Example 13 was 186,480 mPa·s.

Tables 3–5 show that the emulsions with the highest viscosity were the emulsions of Examples 8–13 in which the silicone latex was added to the water phase.

Other variations may be made in compositions and methods described herein without departing from the essential features of the invention. The embodiments of the invention specifically illustrated herein are exemplary only and not intended as limitations on their scope except as defined in the appended claims.

What is claimed is:

1. A method of making a water-in-silicone emulsion comprising the steps of (i) preparing a silicone phase containing a silicone polyether and a cyclic siloxane; (ii) preparing an aqueous phase containing water and at least one cosmetically acceptable personal care component as an active ingredient; (iii) adding a silicone latex to the aqueous phase; (iv) combining the silicone phase with the aqueous phase containing the silicone latex; and (v) mixing the combined phases until an emulsion is formed; the silicone phase comprising 20–80 percent by weight of the emulsion, and the aqueous phase comprising 20–80 percent by weight of the emulsion, based on the total weight of the emulsion.

2. A method according to claim 1 in which the cosmetically acceptable personal care component is an antiperspirant salt, a humectant, an organic surfactant, an electrolyte, or a preservative.

3. A method according to claim 1 in which the silicone latex is a composition prepared by:

(A) mixing (i) 100 weight parts of a siloxane polymer having a viscosity of greater than 5,000 mPa·s but less than 500,000 mPa·s at 25° C., (ii) 0.5–10 weight parts of a surfactant, and (iii) 0.5–25 weight parts of water; (B) emulsifying the mixture into a gel phase having a siloxane polymer content of at least 80% by weight; (C) diluting the emulsion with further water to a siloxane polymer content of at least 75% by weight; (D) adding 0.00001–20 weight parts catalyst either before or after the emulsification, or before or after the dilution; (E) adding 0.1–20 weight parts crosslinker either before or after the emulsification, or before or after the dilution; and (F) or in place of adding (D) and (E), adding 1–5 weight parts self catalytic crosslinker either before or after emulsification, or before or after dilution.

4. A method according to claim 1 in which the silicone polyether is a composition having the formula:

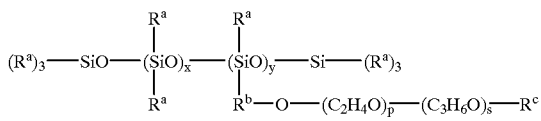

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, or an aryl group; m has a value of two to eight; p and s have values such that the oxyalkylene segment $-(C_2H_4O)_p-(C_3H_6O)_s-$ has a molecular weight in the range of 400 to 5,000; the segment having 50–99 mole percent of oxyethylene units $-(C_2H_4O)_p-$ and 1–50 mole percent of oxypropylene units $-(C_3H_6O)_s-$; x has a value of 80 to 400; and y has a value of 2 to 10.

5. A method according to claim 1 in which the silicone phase further contains a silicone elastomer prepared by a crosslinking reaction between an $\equiv$Si—H containing polysiloxane and an alpha, omega-diene, carried out in the presence of a platinum catalyst and a cyclic siloxane.

6. A method according to claim 1 in which the silicone phase further contains a pigment.

7. A method according to claim 1 in which the silicone phase contains 0.2–2.0 percent by weight of the silicone polyether, and the balance of the silicone phase to 100 percent is the cyclic siloxane.

8. A method according to claim 1 in which the aqueous phase includes 0.1–5.0 percent by weight of the silicone latex.

9. A water-in-silicone emulsion prepared according to the method defined in claim 1.

* * * * *